United States Patent [19]

Bock et al.

[11] 4,324,879

[45] Apr. 13, 1982

[54] PROCESS FOR THE PREPARATION OF POLYISOCYANATES CONTAINING ISOCYANURATE GROUPS AND THE USE THEREOF

[75] Inventors: Manfred Bock, Leverkusen; Josef Pedain, Cologne; Walter Uerdingen, Leverkusen, all of Fed. Rep. of Germany

[73] Assignee: Bayer Aktiengesellschaft, Leverkusen, Fed. Rep. of Germany

[21] Appl. No.: 151,005

[22] Filed: May 19, 1980

Related U.S. Application Data

[63] Continuation of Ser. No. 69,412, Aug. 24, 1979, abandoned.

[30] Foreign Application Priority Data

Sep. 8, 1978 [DE] Fed. Rep. of Germany ....... 2839133

[51] Int. Cl.$^3$ ..................... C08G 18/20; G08G 18/80; C08G 18/79
[52] U.S. Cl. ........................................ 528/45; 528/52; 528/67; 528/73; 544/193; 544/196; 260/453 P
[58] Field of Search .................... 528/52, 67, 73, 45; 544/193, 196

[56] References Cited

U.S. PATENT DOCUMENTS

| | | | |
|---|---|---|---|
| 3,010,963 | 11/1961 | Erner ...................................... | 528/54 |
| 3,042,632 | 7/1962 | Erner ...................................... | 528/52 |
| 3,211,703 | 10/1965 | Gilman et al. ..................... | 260/77.5 |
| 3,330,828 | 7/1967 | Grogler et al. ..................... | 260/248 |
| 3,487,080 | 12/1969 | Matsui et al. ....................... | 260/248 |
| 3,583,943 | 6/1971 | Weber et al. .......................... | 528/73 |
| 3,892,687 | 7/1975 | Bechara et al. ............... | 260/2.5 AC |
| 3,995,997 | 12/1976 | Boehinke et al. .......................... | 8/54 |
| 4,115,373 | 9/1978 | Henes et al. ........................... | 528/73 |

FOREIGN PATENT DOCUMENTS

| | | |
|---|---|---|
| 1150080 | 12/1963 | Fed. Rep. of Germany . |
| 809809 | 3/1959 | United Kingdom . |
| 952931 | 3/1964 | United Kingdom . |
| 966338 | 8/1964 | United Kingdom . |
| 1402659 | 8/1975 | United Kingdom . |

OTHER PUBLICATIONS

DAS 1,013,869, Bayer A/G, Aug. 14, 1957.
DAS 2,226,191, Bayer A/G, Dec. 13, 1973.
DOS 2,325,826, Veba-Chemie, Dec. 19, 1974.
DOS 2,616,415, BASF A/G, Nov. 3, 1977.
DOS 2,644,684, Veba-Chemie, Apr. 6, 1978.

*Primary Examiner*—H. S. Cockeram
*Attorney, Agent, or Firm*—Gene Harsh; Lawrence S. Pope; Thomas W. Roy

[57] ABSTRACT

The present invention is concerned with an improved process for the production of partially trimerized hexamethylene diisocyanate which yields isocyanurate isocyanates which have low viscosity and low monomer contents by the use of a quaternary ammonium hydroxide catalyst which is hydroxyalkyl substituted at its N atom.

9 Claims, No Drawings

PROCESS FOR THE PREPARATION OF POLYISOCYANATES CONTAINING ISOCYANURATE GROUPS AND THE USE THEREOF

This is a continuation, of application Ser. No. 69,412 filed Aug. 24, 1979, now abandoned.

FIELD OF THE INVENTION

The present invention relates to a novel process for the preparation of solvent-free polyisocyanates containing isocyanurate groups by the partial trimerization of the isocyanate groups of hexamethylene diisocyanate.

BACKGROUND OF THE INVENTION

Polyurethane lacquers which are stable to light and which are free from solvent or contain only a small amount of solvent require low viscosity, colorless or only slightly colored polyisocyanates with a high isocyanate content.

Low viscosity polyisocyanates which are formed by the polymerization of hexamethylene diisocyanate are potentially very suitable for this purpose. Hexamethylene diisocyanate is a product which is readily available commercially, and the polymerization thereof, to form a polyisocyanate containing isocyanurate groups has been known for a long time from the literature. However, the polymers of hexamethylene diisocyanate (hereinafter known as HDI) containing NCO groups, which are obtained by the known production processes, are unsuitable or are only suitable to a limited extent for use in the production of lacquers which are stable to light and which are free from solvent or contain only a small amount of solvent.

Thus, for example, the HDI polymers which can be obtained in accordance with German Offenlegungsschrift No. 2,616,415 cannot meet all the requirements of lacquer polyisocyanates for high quality polyurethane lacquers, in spite of their relatively low viscosity, owing to their intrinsic color which leads to discoloration of the lacquer coatings. The same applies to the HDI polymer described in German Auslegeschrift No. 2,226,191, in column 5, line 55 to column 6, line 6. The last-mentioned HDI polymer also has a high content of dimerized HDI. Owing to the splitting up of this dimeric HDI, more free HDI is formed very easily during storage of the polyisocyanate so that, after sometime, the product has a high content of free HDI.

Other known processes for the polymerization of HDI use metal compounds as catalysts, for example, alkali metal or lead salts. According to British Pat. No. 809,809, these catalysts have the advantage that they lead to products which contain little or no dimeric material. Catalysts with metal compounds does however have several disadvantages. Since this reaction takes place quite vigorously, high viscosity, in part inhomogeneous products with a low NCO content are formed (cf. U.S. Pat. No. 3,330,828—Example 6; British Pat. No. 925,931—Example 2; or German Ausleseschrift No. 1,013,869—Example 4).

Owing to the exothermal reaction which takes place inhomogeneously, particles of gel which can be removed with difficulty only after being diluted with solvent, are also produced during metal catalysis (British Pat. No. 966,338). Another substantial disadvantage of the metal compounds recommended as catalyst in the publications is that when the catalysis is stopped, inorganic salts are formed which are insoluble in the polyisocyanate and cause haze and can also only be removed after dilution with a large amount of solvent, if at all.

According to the process described in U.S. Pat. No. 3,211,703, the reaction product during the polymerization of HDI is also either a gel or occurs in a dilute solution and cannot therefore be used in lacquers which are free from solvent or low in solvent. U.S. Pat. No. 3,211,703 does not disclose how HDI could be trimerized to form a liquid, solvent-free polyisocyanate. The same applies to German Offenlegungsschrift No. 2,644,684. In that specification, the same catalyst system of an alkylene oxide and N,N'-endoethylene piperazine is recommended, in particular for the polymerization of cycloaliphatic isocyanates as in U.S. Pat. No. 3,211,703. Moreover, the teaching in German Offenlegungsschrift No. 2,644,684 does not go beyond the disclosure in U.S. Pat. No. 3,211,703.

In German Offenlegungsschrift No. 2,325,826, aziridine or an aziridine derivation in combination with a tertiary amine is recommended for the catalysis of the trimerization of isocyanate groups. Apart from the disadvantage of the simultaneous use of solvents, the process in the last-mentioned Offenlegungsschrift has the particular disadvantage that poisonous catalysts which are known to be carcinogenic have to be used. The long incubation period of the polymerization reaction is another disadvantage.

According to German Auslegeschrift No. 1,150,080, quaternary ammonium hydroxides are used as catalysts for the trimerization of isocyanates. As illustrated by the embodiments in this publication, the above-mentioned catalysts are in practice used only for the polymerization of aromatic isocyanates. Attempts to polymerize aliphatic isocyanates and, in particular, HDI in accordance with the teaching in that Auslegeschrift, in the absence of solvents lead to inhomogeneous reaction products which cannot be used as the isocyanate component in high quality polyurethane lacquers. The unsuitability of the catalysts recommended in the Auslegeschrift referred to for the trimerization of aliphatic isocyanates is also revealed by Example 13 in which the trimerization of n-hexadecyl isocyanate only leads to a yield of the corresponding trimerizate laying below 50%, even after a reaction time of 4 days.

It can be seen from the foregoing that no process which can be carried out commercially in a simple manner and which allows the problem-free preparation of virtually colorless, low-viscosity, solvent-free polyisocyanates, containing isocyanurate groups, based on HDI, has yet been disclosed. Accordingly, an object of the present invention was to provide such a process.

This object could surprisingly be accomplished in accordance with process of this invention by using ammonium hydroxides carrying hydroxyalkyl substituents at the nitrogen atom as catalyst for the trimerisation of the isocyanate groups. This possibility to solve the problem of the invention is surprising since it has been known from U.S. Pat. No. 3,487,080 that such special ammonium hydroxides are unsuitable catalysts for the trimerisation of toluylene diisocyanates (TDI) which are known to be much more reative than hexamethylene diisocyanate (HDI). Thus it is clear from table 3 of said U.S. Patent that i.e. β-hydroxyethyl-trimethylammonium hydroxide is no catalyst for the trimerisation of TDI since the gelation time is indicated to be more than 4320 minutes. According to U.S. Pat. No.

3,487,080 it is therefore absolutely necessary to use such catalysts together with a second catalyst component.

SUMMARY OF THE INVENTION

The present invention therefore relates to a process for the preparation of solvent-free polyisocyanates containing isocyanurate groups, having a viscosity of less than about 10,000 mPas at 25° C. and a monomeric diisocyanate content of less than about 3% by weight, by partial trimerization of the isocyanate groups of hexamethylene diisocyanate in the presence at least of one quaternary ammonium hydroxide as catalyst and separation known per se of excess, unreacted diisocyanate and optionally solvent used, characterized in that an ammonium hydroxide which is hydroxyalkyl-substituted at the nitrogen atom is used as quaternary ammonium hydroxide.

In the process according to the invention, in contrast to the process in German Pat. No. 1,150,080 quaternary ammonium hydroxides which are hydroxyalkyl-substituted at the nitrogen atom are used as catalysts.

DETAILED DESCRIPTION OF THE INVENTION

In the process according to the invention, the quaternary ammonium hydroxides to be used are those which have a molecular weight of up to 300, preferably 121 to 300, corresponding to the formula

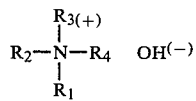

in which
R$_1$ represents an alkyl radical with from 1 to 20, preferably from 4 to 12 carbon atoms, an araliphatic hydrocarbon radical with from 7 to 10, preferably 7 carbon atoms or a saturated cycloaliphatic hydrocarbon radical with from 4 to 10, preferably from 5 to 6 carbon atoms.

R$_2$, R$_3$, and R$_4$ which may be the same or different, represents alkyl radicals containing from 1 to 20, preferably from 1 to 4 carbon atoms, in which two of the radicals R$_2$, R$_3$ or R$_4$ together with nitrogen atom and optionally together with an oxygen hetero atom or another nitrogen hetero atom can form a heterocyclic ring containing from 3 to 5 carbon atoms, or wherein the R$_2$, R$_3$ and R$_4$ radicals each represent ethylene radicals which, together with the quaternary nitrogen atom and an additional tertiary nitrogen atom can form a bicyclic triethylene-diamine framework, with the proviso that at least one of the radicals R$^1$, R$^2$, R$^3$ or R$^4$ contains at least one aliphatically bonded hydroxyl group which is preferably arranged in the 2-position to the quaternary nitrogen atom, wherein the hydroxyl-substituted radical or the hydroxyl-substituted radicals may also contain further substituents, in particular C$_1$–C$_4$-alkoxy-substituents in addition to the hydroxyl substituents.

Particularly preferred quaternary ammonium hydroxides which are to be used according to the invention include those corresponding to the above-mentioned formula, in which the R$_1$ and R$_3$ radicals each represent alkyl radicals of the specified type/and R$_4$ represents a hydroxyethyl, hydroxylpropyl or hydroxybutyl radical in which the hydroxyl group is preferably arranged in the 2-position to the quaternary nitrogen.

Examples of suitable quaternary ammonium hydroxides include

N-(2-hydroxyethyl)-N,N-dimethyl-N-(2,2'-dihydroxy-methylbutyl)ammonium hydroxide; N,N,N-trimethyl-N-(2-hydroxyethyl)ammonium hydroxide; N-methyl-2-hydroxyethyl-morpholinium hydroxide; N-methyl-N-(2-hydroxypropl)-pyrrolidinium hydroxide; N,N,N-trimethyl-N-(2-hydroxypropyl)ammonium hydroxide; N,N,N-trimethyl-N-(2-hydroxybutyl)ammonium hydroxide; tetra-(2-hydroxyethyl)-ammonium hydroxide or the compound corresponding to the formula

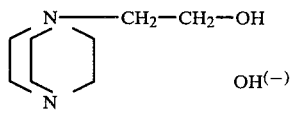

which represents the monoadduct of ethylene oxide and water to 1,4-diazabicyclo-(2,2,2)-octane.

The quaternary ammonium hydroxides to be used according to the invention and the production thereof are known. The preferred hydroxyalkyl-substituted ammonium hydroxides are prepared in a manner known per se by reacting alkylene oxide with tertiary amines in an aqueous alcoholic medium (cf. U.S. Pat. No. 3,995,997, incorporated herein by reference, column 2, particularly lines 19–44).

As already mentioned the simultaneous use of an additional co-catalyst is not necessary although the simultaneous use of a co-catalyst as i.e. the known Mannich bases or quaternary ammonium hydroxides which do not carry hydroxyalkyl substituents is possible.

The catalysts to be used according to the invention are preferably used, dissolved in suitable solvents. Toluene, dimethyl formamide, dimethyl sulphoxide or even mixtures of these solvents, for example, are suitable solvents, depending upon the type of catalyst. It is also possible to use hydroxy compounds as solvent for the catalysts which are incorporated into the isocyanate in the form of so-called reactive diluents. Monohydroxy compounds having preferably a molecular weight of above 99 such as i.e. cyclohexanol, 2-ethyl hexanol are as suitable as i.e. glycols such as ethylene glycol, tetramethylene glycol, hexamethylene glycol, 2-ethylhexane-diol-1,3. Methanol is, however, not suitable because it reacts with hexamethylene diisocyanate to form a bis-urethane which cannot be removed by distillation and which forms insoluble sediments at room temperature causing turbidity of the product of the invention. Care must therefore be taken that methanol is absent from the reaction mixture when the process of the invention is carried out. In general the solvents are used in amounts of a maximum of 5% by weight, based on HDI. In the closest approximation, the process according to the invention is generally a "solvent-free" process. The small quantities of solvent which may be used are removed by distillation, together with the excess diisocyanate after the reaction according to the invention provided that they are not incorporated into the product of the process. The use of larger quantities of solvents in the reaction according to the invention, which are removed by distillation after the reaction, is less suitable but is not, however, completely excluded.

In the process according to the invention, the said catalysts are generally used in a quantity of from about 0.01 to 0.6% by weight, preferably of about 0.03 to 0.3% by weight, based on HDI.

The process according to the invention is generally carried out at a temperature of from about 10° to 160° C., preferably from about 20° to 80° C. The amounts of catalyst which have the optimum effect at any time depends on the type of quaternary ammonium compound used. The catalysis according to the invention produces a uniform course of trimerization which is highly selective in the preferred temperature range of from about 20° to 80° C. Incubation does not take place after addition of catalyst. The maximum temperature during exothermal polymerization (trimerization) is not reached in steps, but gradually. This allows the reaction to be monitored well in each phase and also to be controlled in a technically simple manner. Optimum adjustment of reaction period, yield, as well as quality of the HDI isocyanurate is achieved by the concentration of the catalyst system. It has been found that a virtually colorless reaction product having a very desirable viscosity can be obtained by means of the very careful polymerization process according to the invention over a period of, preferably about 2 to 14 hours and subsequent removal by distillation of the solvent optionally used and the excess diisocyanate. An isocyanate of the isocyanurate/HDI solution of from about 34 to 41%, preferably from about 35 to 40%, is described over this period so that isocyanurate yields of between about 30 and 55% can be attained. The viscosity of the final product thus lies below 10,000 mPas. at 25° C. in each case. The thermal instability of the catalyst used is advantageous for the process according to the invention so that the polymerization reaction is terminated when the desired NCO value is attained by heating the isocyanurate solution to temperatures of from about 70° to 120° C., depending upon the type of catalyst used. With quaternary ammonium compounds having a relatively high decomposition temperature, it is advantageous to add to the reaction mixture compounds which deactivate the catalysts. Inorganic acids such as hydrochloric acid, phosphorous acid or phosphoric acid, carboxylic acid halides, such as acetyl chloride or benzoyl chloride, sulphonic acids or their derivatives such as methane sulphonic acid, p-toluene sulphonic acid methyl or ethyl ester and perfluorated compounds such as, for example, nonafluorobutane sulphonic acid, for example, are particularly suitable for this purpose. The last-mentioned compound is preferably used in the case of chemical deactivation. It has the advantage over the conventional inhibitors such as benzoyl chloride or esters of p-toluene sulphonic acid of having no negative influence on the quality of the color of the end product. The inhibitors are used either in pure form or dissolved in solvents such as alcohols or dimethylformamide. It is surprisingly noted when the inhibitors are used that amounts lying far below the equivalence of from about 1 to 50%, preferably from about 5 to 20% of the theoretical amount are required for the purpose inhibiting the reaction. It becomes obvious that, in addition to the expected deactivation by the formation of salt, a reaction initiated by the inhibitors in which the catalysts used are decomposed into ineffective components takes place to an even greater extent. The completion of trimerization in the process according to the invention, either thermally or in the manner described using less than equivalent quantities of inhibitors, results in no haze occurring in the products of the process according to the invention, even when diluted to relatively great extent with the solvents which are conventional in the lacquer art. It is, however, preferred not to use catalyst poisons but to terminate the reaction at the desired degree of trimerisation by thermal desactivation of the catalyst.

The fact that the process according to the invention needs no or only very few inhibitors for the deactivation of the catalyst system is a substantial advantage over all other processes.

It is important for carrying out the process according to the invention to use HDI which is as pure as possible and which is preferably distilled and colorless.

A few general operating instructions are given below:

1. Some HDI is placed in a three-necked flask under a nitrogen atmosphere and reacted with the corresponding amounts of catalyst and optionally cocatalyst successively at 20° to 25° C. with stirring. Trimerization is initiated when the ammonium compound is added, the temperature initially rising to 30° to 35° C. within 15 minutes and subsequently slowly rising to 40° C. to 60° C. within 30 to 90 minutes. This temperature is maintained throughout trimerization. A reduction in the NCO content is determined by titration. After 4 to 6 hours, when the desired NCO value is reached, trimerization is ended either by brief heating to 120° C. or by the addition of a small amount of inhibitor. The clear, almost colorless liquid is then worked up under a high vacuum by thin layer distillation and is freed from excess HDI and any solvent used. A colorless or slightly yellow colored, clear polyisocyanate is obtained as final product. 2. In another variation of the process, some HDI and catalyst pass in a ratio which is suitable for trimerization via metering pumps into a mixing chamber and from there into a reaction cascade at a predetermined temperature of from 50° to 70° C. preferably 55° C. The desired NCO content, which is adjusted rapidly in the cascade, is preferably controlled by the metering of the catalyst. In the final section of the cascade, an inhibitor solution is introduced in a suitable proportion or the reaction is terminated thermally by heating to 120° C. From here, the polymer solution passes into a thin layer evaporator for separation of the excess HDI. The products of the process of the invention exhibit at 25° C. a viscosity of below 10.000 mPas and an NCO content of from about 18 to about 24, preferably from about 20 to about 23% by weight.

The process according to the invention has substantial advantages over the prior art:

The polymerization reaction forming the basis of the process can be carried out slightly exothermally in a short time at a low temperature, i.e., it is energy-saving and, at the same time very easy to control. The catalysts can be deactivated thermally or by means of a very small quantity of an inhibitor which corresponds to less than the equivalent quantity. The products of the process are stable and do not release any free HDI during storage as they contain virtually no uretdione groups. The product colorless and has a high NCO content and a low viscosity. In particular, the slight natural color of the products of the process according to the invention allows them to be used as isocyanate components in high quality polyurethane lacquers. The products of the process according to the invention are particularly well suited to the production of single-component and bi-component polyurethane lacquers which are free from solvent or low in solvent. In this case, the products of the process according to the invention can be used both as they are and in the form in which the isocyanate groups are blocked with blocking agents.

Preferred reactants for the products of the process according to the invention which may be present in blocked form during the production of polyurethane lacquers include the polyhydroxy polyesters and polyethers, polyhydroxy polyacrylates and optionally polyhydric alcohols of lower molecular weight, which are known per se in the polyurethane lacquer art. Polyamines, in particular in blocked form as polyketimines or oxazolidines are also possible reactants for the products of the process according to the invention. The proportions in which the optionally blocked polyisocyanates according to the invention and the specified reactants are reacted during the production of polyurethane lacquers are generally selected so that about 0.8 to 3, preferably about 0.9 to 1.1, hydroxyl, amino and/or carboxyl groups are allocated to one (optionally blocked) isocyanate group.

The catalysts which are conventional in isocyanate chemistry can be used in known manner to accelerate curing, such as, for example, tertiary amines such as triethylamine, pyridine, methyl pyridine, benzyl dimethyl amine, N,N-dimethyl amino-cyclohexane, N-methyl piperidine, pentamethyl diethylene triamine, N,N'-endoethylene piperazine, N,N'-dimethyl piperazine, etc., metal salts such as iron(III)-chloride, zinc chloride, zinc-2-ethyl caproate, tin(II)-2-ethyl caproate, dibutyl tin(IV)-dilaurate, molybdenum glycolate etc.

When the products of the process according to the invention are used in stoved lacquers, the isocyanate groups are wholly or partially blocked in known manner. The polyisocyanate is reacted with a suitable blocking agent, preferably at elevated temperature (for example, from 40° to 140° C.), optionally in the presence of a suitable catalyst such as, for example, tertiary amines, metal salts such as zinc-2-ethyl caproate, tin(II)-2-ethylcaproate, dibutyl tin(IV)-dilaurate or alkali phenolate.

Suitable blocking agents include, for example: monophenols such as phenol, the cresols, the trimethylphenols, the tertiary butyl phenols; tertiary alcohols such as tertiary butanol, tertiary amyl alcohol, dimethylphenyl carbonyl; compounds which readily form enols such as acetoacetic ester, acetyl acetone, malonic acid derivatives such as malonic acid diester having from 1 to 8 carbon atoms in the alcohol radicals; secondary aromatic amines such as N-methyl aniline, the N-methyl toluidines, N-phenyl-toluidine, N-phenyl xylidine; imides such as succinimide; lactams such as ε-caprolactam, δ-valerolactam; oximes such as butanone oximines, cyclohexanone oxime; mercaptans such as methyl mercaptans, ethyl mercaptan, butyl mercaptan, 2-mercapto benzthiazole, -naphthyl mercaptan, dodecyl mercaptan, triazoles such as 1H-1,2,4-triazole.

In order to produce the lacquer binder, blocked polyisocyanate, polyfunctional reactant, catalyst and optionally the conventional additives such as, for example, pigments, dyes, fillers and eluants are optionally thoroughly mixed and homogenized with each other on a conventional mixing unit such as, for example, on a sand mill either with or without solvent and diluent.

The painting and coating agents can be applied to the article to be coated in solution or from the melt or in solid form, by the conventional methods such as for example, brushing, rolling, pouring, injecting, by the whirling sinter method or by the electrostatic powder spraying method.

The lacquers containing the polyisocyanates according to the invention produce films which adhere surprisingly well to a metallic substrate and which are particularly fast to light, thermally stable to coloration and very resistant to abrasion. In addition, they are distinguished by their great hardness, elasticity, very good resistance to chemicals, high lustre, excellent weather resistance and good affinity for pigments.

The following examples illustrate the invention. All percentages relate to percentages by weight. In the following examples catalyst solutions I, II and III are used. These catalysts were prepared in an aqueous solution according to U.S. Pat. No. 3,995,997. Water and other volatile constituents are distilled off under vacuum. The distillation residue is then dissolved in 2-ethylhexanol.

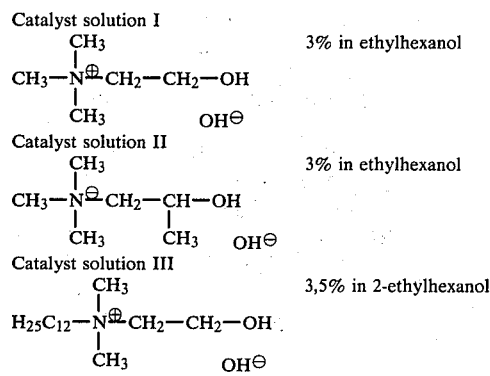

EXAMPLE 1

50.5 kg of hexamethylene diisocyanate are admixed in a reaction vessel with 750 ml of catalyst solution I. The temperature of the reaction mixture rises within 1 hour to about 43° to about 48° C. When this exothermic reaction has come to a standstill the NCO content of the liquid was 47%. The reaction vessel is now heated to about 47° to 50° C. The temperature of the reaction mass rises to about 53° to about 56° C. The NCO content of the reaction product decreases by 1.2% per hour. When the NCO content reaches about 40 to about 41% the reaction is stopped by heating the mixture to 120° C. The reaction mixture is filtered and submitted to a thin film distillation. The residue consisted of 15 kg of a colorless liquid polyisocyanate having an NCO content of 21.8%, a viscosity at 25° C. of 2100 mPas and a content of monomeric HDI of 0.3%.

EXAMPLE 2

1,344 kg of HDI and 45 ml of the catalyst solution II are admixed in the mixing vessel of a cascade consisting of said mixing vessel and two reaction vessels which can be heated. The temperature in the mixing vessel rises to 35° C. The first reaction vessel is heated to 55° C. and the second reaction vessel is heated to 60° C. In the course of the continuous reaction the polymerisation is controlled by determination of the NCO content. The NCO content in the first reaction vessel centered around 44.5 to 45.5% and in the second reaction vessel around 38 to about 40%. The average residence time in the cascade is 4 hours. The raw product is removed from the cascade through a heating apparatus where the reaction is stopped by heating to 100° to 120° C. Finally the reaction mixture is submitted to a thin film distillation apparatus where excess HDI is removed under vacuum at 140° to 160° C. The product of this continuous process is practically colorless. It is clear and exhibits following properties:

NCO content: 21.0%,
monomeric HDI: 0.25%,
viscosity (25° C.): 3100 mPas.

EXAMPLE 3

As in example 1 1344 g of hexamethylene diisocyanate are admixed at 45° C. with 50 g of catalyst solution III. The temperature of the reaction mixture rises within 2 hours to 57° C. Subsequently another 5 g of catalyst solution III are added and the reaction mixture is heated for 2 hours to 60° C. The NCO content of the reaction mixture is then determined to be 41%. Subsequently 1 half of the reaction mixture is heated 100° C. and maintained at this temperature for 15 minutes. Subsequently excess HDI is removed under vacuum in a thin film distillation apparatus at 140° to 160° C. The distillation residue is a clear, light-yellow liquid which exhibits an NCO content of 21.9%, a viscosity at 25° C. of 3000 mPas and a content of monomeric HDI of 0.5%.

The second half of the reaction mixture is admixed with the solution of 0.2 g of nonafluor-butane sulfonic acid in 1 ml of dimethyl formamide and subsequently submitted to the same thin film distillation. Hereagain a low-viscous light-coloured product having an NCO content of 22.1% is obtained.

What is claimed is:

1. A process for the preparation of clear and substantially colorless or slightly colored, solvent-free polyisocyanates containing isocyanurate groups, having a viscosity of less than about 10,000 mPas at 25° C. and a monomeric diisocyanate content of less than about 3% by weight, comprising partially trimerizing the isocyanate groups of hexamethylene diisocyanate in the presence of at least one quaternary ammonium hydroxide as catalyst and subsequently separating excess, unreacted diisocyanate and solvent which may be used, said process characterized in that an ammonium hydroxide which is hydroxyalkyl substituted at the nitrogen atom is used as the quaternary ammonium hydroxide.

2. Process according to claim 1 wherein the reaction is terminated at the desired degree of trimerisation by thermal deactivation of the catalyst at 70° to 120° C.

3. The process of claim 1 wherein said quaternary ammonium hydroxide is N,N,N-trimethyl-N-(2-hydroxyethyl)-ammonium hydroxide.

4. The process of claim 1 wherein said quaternary ammonium hydroxide is N,N,N-trimethyl-N-(2-hydroxypropyl)-ammonium hydroxide.

5. The process of claim 1 wherein said quaternary ammonium hydroxide is N,N-dimethyl-N-dodecyl-N-(2-hydroxyethyl)-ammonium hydroxide.

6. The process of claim 1 wherein said quaternary ammonium hydroxide is N-methyl-N-(2-hydroxypropyl)-pyrrolidinium hydroxide.

7. The process of claim 1 wherein said quaternary ammonium hydroxide is N-methyl-(2-hydroxyethyl)-morpholinium hydroxide.

8. In the process for the preparation of polyurethane lacquers from reactants comprising an isocyanate-containing component, the improvement comprising preparing at least a portion of the isocyanate-containing component by the process of claim 1 or 2.

9. The process of claim 8 wherein at least a portion of the isocyanate groups of said isocyanate-containing component are blocked with a blocking agent.

* * * * *